(12) United States Patent
Behnke

(10) Patent No.: US 10,828,100 B2
(45) Date of Patent: Nov. 10, 2020

(54) MICROWAVE ABLATION WITH TISSUE TEMPERATURE MONITORING

(75) Inventor: Robert J. Behnke, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 1352 days.

(21) Appl. No.: 12/547,155

(22) Filed: Aug. 25, 2009

(65) Prior Publication Data

US 2011/0054458 A1 Mar. 3, 2011

(51) Int. Cl.
*A61B 18/18* (2006.01)
*A61B 18/00* (2006.01)
*A61B 17/00* (2006.01)

(52) U.S. Cl.
CPC .......... *A61B 18/18* (2013.01); *A61B 18/1815* (2013.01); *A61B 2017/00026* (2013.01); *A61B 2017/00084* (2013.01); *A61B 2018/00577* (2013.01); *A61B 2018/00642* (2013.01); *A61B 2018/00678* (2013.01); *A61B 2018/00702* (2013.01); *A61B 2018/00714* (2013.01); *A61B 2018/00779* (2013.01); *A61B 2018/00791* (2013.01); *A61B 2018/00875* (2013.01)

(58) Field of Classification Search
CPC .......... A61B 2018/00642; A61B 2018/00678; A61B 2018/00702; A61B 2018/00714; A61B 2018/00791; A61B 2018/00779; A61B 2018/00875; A61B 2018/1823; A61B 2018/1892; A61B 18/18; A61B 18/1815; A61B 2017/00026; A61B 2017/00084
USPC ...................................... 606/32–33; 607/101
See application file for complete search history.

(56) References Cited

U.S. PATENT DOCUMENTS

| | | | |
|---|---|---|---|
| 4,204,549 A | 5/1980 | Paglione |
| 4,291,708 A | 9/1981 | Frei et al. |
| 4,612,940 A | 9/1986 | Kasevich et al. |
| 4,672,980 A | 6/1987 | Turner |
| 4,934,365 A | 6/1990 | Morgenthaler |
| 4,960,109 A | 10/1990 | Lele |
| 4,967,765 A | 11/1990 | Turner et al. |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael F Peffley
*Assistant Examiner* — Samantha M Good

(57) ABSTRACT

A microwave ablation system for treating tissue includes at least first and second antennas, a microwave output stage, and a sensor component. The at least first and second antennas are adapted for insertion into tissue. The microwave output stage is adapted to generate microwave energy and is operatively coupled to at least the first antenna to transmit the microwave energy into the tissue. The sensor component is operatively coupled to the first and second antennas and operatively monitors the microwave energy therebetween.

18 Claims, 6 Drawing Sheets

(56) References Cited

U.S. PATENT DOCUMENTS

| | | | |
|---|---|---|---|
| 5,057,106 A | 10/1991 | Kasevich et al. |
| 5,097,846 A | 3/1992 | Larsen |
| 5,220,927 A | 6/1993 | Astrahan et al. |
| 5,344,435 A | 9/1994 | Turner et al. |
| 5,354,325 A * | 10/1994 | Chive .................... A61B 18/18 |
| | | | 607/101 |
| 5,462,521 A | 10/1995 | Brucker et al. |
| 5,558,672 A | 9/1996 | Edwards et al. |
| 5,569,241 A | 10/1996 | Edwards |
| 5,609,151 A | 3/1997 | Mulier et al. |
| 5,643,197 A | 7/1997 | Brucker et al. |
| 5,672,173 A | 9/1997 | Gough et al. |
| 5,683,384 A | 11/1997 | Gough et al. |
| 5,735,847 A | 4/1998 | Gough et al. |
| 5,800,484 A | 9/1998 | Gough et al. |
| 5,810,804 A | 9/1998 | Gough et al. |
| 5,843,021 A | 12/1998 | Edwards et al. |
| 5,863,290 A | 1/1999 | Gough et al. |
| 5,904,709 A | 5/1999 | Arndt et al. |
| 5,951,547 A | 9/1999 | Gough et al. |
| 5,964,755 A | 10/1999 | Edwards |
| 6,016,452 A | 1/2000 | Kasevich |
| 6,019,757 A | 2/2000 | Scheldrup |
| 6,056,744 A | 5/2000 | Edwards |
| 6,059,780 A | 5/2000 | Gough et al. |
| 6,080,150 A | 6/2000 | Gough |
| 6,097,985 A | 8/2000 | Kasevich et al. |
| 6,106,524 A | 8/2000 | Eggers et al. |
| 6,134,476 A | 10/2000 | Arndt et al. |
| 6,167,313 A | 12/2000 | Gray et al. |
| 6,175,768 B1 | 1/2001 | Arndt et al. |
| 6,181,970 B1 | 1/2001 | Kasevich |
| 6,188,930 B1 | 2/2001 | Carson |
| 6,233,490 B1 | 5/2001 | Kasevich |
| 6,290,715 B1 | 9/2001 | Sharkey et al. |
| 6,347,251 B1 | 2/2002 | Deng |
| 6,350,276 B1 | 2/2002 | Knowlton |
| 6,413,255 B1 | 7/2002 | Stern |
| 6,416,491 B1 | 7/2002 | Edwards et al. |
| 6,425,912 B1 | 7/2002 | Knowlton |
| 6,430,446 B1 | 8/2002 | Knowlton |
| 6,470,217 B1 | 10/2002 | Fenn et al. |
| 6,477,426 B1 | 11/2002 | Fenn et al. |
| 6,485,486 B1 | 11/2002 | Trembly et al. |
| 6,514,249 B1 | 2/2003 | Maguire et al. |
| 6,547,788 B1 | 4/2003 | Maguire et al. |
| 6,569,162 B2 | 5/2003 | He |
| 6,575,969 B1 | 6/2003 | Rittman, III et al. |
| 6,582,425 B2 | 6/2003 | Simpson |
| 6,613,047 B2 | 9/2003 | Edwards |
| 6,622,731 B2 | 9/2003 | Daniel et al. |
| 6,666,862 B2 | 12/2003 | Jain et al. |
| 6,673,070 B2 | 1/2004 | Edwards et al. |
| 6,690,976 B2 | 2/2004 | Fenn et al. |
| 6,699,241 B2 | 3/2004 | Rappaport et al. |
| 6,706,040 B2 | 3/2004 | Mahon et al. |
| 6,723,091 B2 | 4/2004 | Goble et al. |
| 6,725,095 B2 | 4/2004 | Fenn et al. |
| 6,752,767 B2 | 6/2004 | Turovskiy et al. |
| 6,752,804 B2 | 6/2004 | Simpson et al. |
| 6,788,977 B2 | 9/2004 | Fenn et al. |
| 6,796,980 B2 | 9/2004 | Hall |
| 6,807,444 B2 | 10/2004 | Tu et al. |
| 6,869,431 B2 | 3/2005 | Maguire et al. |
| 6,944,504 B1 | 9/2005 | Arndt et al. |
| 6,955,675 B2 | 10/2005 | Jain |
| 6,974,463 B2 | 12/2005 | Magers et al. |
| 7,025,765 B2 | 4/2006 | Balbierz et al. |
| 7,108,696 B2 | 9/2006 | Daniel et al. |
| 7,160,296 B2 | 1/2007 | Pearson et al. |
| 7,200,445 B1 | 4/2007 | Dalbec et al. |
| 7,204,832 B2 | 4/2007 | Altshuler et al. |
| 7,267,683 B2 | 9/2007 | Sharkey et al. |
| 7,278,991 B2 | 10/2007 | Morris et al. |
| 7,282,061 B2 | 10/2007 | Sharkey et al. |
| 7,293,562 B2 | 11/2007 | Malecki et al. |
| 7,300,436 B2 | 11/2007 | Penny et al. |
| 7,300,438 B2 | 11/2007 | Falwell et al. |
| 7,344,533 B2 | 3/2008 | Pearson et al. |
| 7,367,975 B2 | 5/2008 | Malecki et al. |
| 7,377,917 B2 | 5/2008 | Trembly |
| 7,400,930 B2 | 7/2008 | Sharkey et al. |
| 7,419,487 B2 | 9/2008 | Johnson et al. |
| 7,422,586 B2 | 9/2008 | Morris et al. |
| 7,468,042 B2 | 12/2008 | Turovskiy et al. |
| 2002/0120261 A1 | 8/2002 | Morris et al. |
| 2002/0165529 A1 | 11/2002 | Danek |
| 2004/0186468 A1* | 9/2004 | Edwards ........................ 606/41 |
| 2005/0033278 A1 | 2/2005 | McClurken et al. |
| 2005/0137662 A1 | 6/2005 | Morris et al. |
| 2005/0240239 A1 | 10/2005 | Boveja et al. |
| 2006/0015162 A1 | 1/2006 | Edward et al. |
| 2006/0030914 A1 | 2/2006 | Eggers et al. |
| 2006/0047275 A1* | 3/2006 | Goble ............................ 606/37 |
| 2007/0198006 A1 | 8/2007 | Prakash et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |

(56) References Cited

FOREIGN PATENT DOCUMENTS

| | | |
|---|---|---|
| FR | 2 864 439 | 7/2005 |
| GB | 2416307 A | 1/2006 |
| JP | H02185267 A | 7/1990 |
| JP | 5-5106 | 1/1993 |
| JP | 05-40112 | 2/1993 |
| JP | 6-503028 | 4/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2002-523127 A | 7/2002 |
| JP | 2005-503864 A | 2/2005 |
| SU | 166452 | 11/1964 |
| SU | 401367 | 11/1974 |
| SU | 727201 | 4/1980 |
| WO | WO 97/006739 | 2/1997 |
| WO | WO 97/006740 | 2/1997 |
| WO | WO 97/006855 | 2/1997 |
| WO | WO 99/01074 | 1/1999 |
| WO | WO 99/22657 | 5/1999 |
| WO | WO 99/44520 | 9/1999 |
| WO | WO 00/053113 | 9/2000 |
| WO | WO 00/54682 | 9/2000 |
| WO | WO 03/047043 | 6/2003 |
| WO | WO 03/088806 | 10/2003 |
| WO | WO 06/105121 | 10/2006 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.

(56) References Cited

OTHER PUBLICATIONS

Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N. J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Dec. 1999) "FlexStrand": product description, 1 page.
Mdtech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.

(56) References Cited

OTHER PUBLICATIONS

European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report for EP 10 00 8850 dated Nov. 30, 2010.
Japanese Office Action and English Translation for JP 2015-007508 dated Nov. 17, 2015.
Japanese Office Action dated Jul. 26, 2016 in corresponding Japanese Patent Application No. 2015-007508, together with an English translation, 6 pages.

* cited by examiner

MICROWAVE ABLATION WITH TISSUE TEMPERATURE MONITORING

BACKGROUND

1. Technical Field

The present disclosure relates to microwave ablation. More particularity, the present disclosure relates to a system and method of monitoring tissue temperature during surgery utilizing microwave ablation antennas.

2. Description of Related Art

Historically, surgery was performed using only mechanical tools, such as mechanical cutting instruments, scalpels, bladed forceps, saws and the like. However, in recent years, technology has improved such that surgeons now frequently use electromagnetic waves to cause a wider variety of surgical effects, e.g., by selectively modifying tissue using electromagnetic energy to produce a specific tissue result. The characteristics of the electromagnetic energy applied to tissue strongly correlates to the effect that the energy has on the tissue. These characteristics are therefore changed in accordance with the desired tissue outcome. A type of electromagnetic energy commonly applied during surgery is microwave energy.

Treatment of certain diseases requires destruction of tissue (e.g., tumors) or some surrounding tissue. For example, it is known that tumor cells denature at elevated temperatures that are slightly lower than temperatures injurious to surrounding healthy cells. Therefore, known treatment methods, such as hypertheimia therapy, heat tumor cells to temperatures above 41° C. while maintaining adjacent healthy cells at lower temperatures to avoid irreversible cell damage. Such methods involve applying microwave energy the tissue. In particular, microwave energy is used to coagulate or ablate tissue. Another method used to treat diseased tissue is to resect a portion of the diseased organ, tissue or anatomical structure. For example, a liver may contain diseased tissue and healthy tissue. One treatment option is to pre-coagulate and ablate some of the liver tissue to facilitate resection of a portion of the liver including the diseased tissue. Microwave energy can be used during these types of procedures to pre-coagulate tissue prior to resection, to reduce bleeding during resection and to facilitate the actual resection of the tissue.

The microwave energy may be applied to tissue via antennas that can penetrate tissue. There are several types of microwave antennas, such as monopole and dipole antennas. In monopole and dipole antennas, most of the microwave energy radiates perpendicularly away from the axis of the conductor. A monopole antenna includes a single, elongated conductor that transmits the microwave energy. A typical dipole antenna has two elongated conductors parallel to each other and positioned end-to-end relative to one another with an insulator placed therebetween. Each of the conductors is typically about ¼ of the length of the wavelength of the microwave energy making the aggregate length of both conductors about ½ of the wavelength of the microwave energy.

SUMMARY

The present disclosure relates to microwave ablation. More particularly, the present disclosure relates to a system and method of monitoring tissue temperature during surgery utilizing microwave ablation antennas.

In one embodiment of the present disclosure, a microwave ablation system for treating tissue includes first and second antennas, a microwave output stage, and a sensor component. The at least first and second antennas are adapted for insertion into tissue. The microwave output stage is adapted to generate microwave energy and is operatively coupled to at least the first antenna to transmit the microwave energy into the tissue. The sensor component is operatively coupled to the first and second antennas and operatively monitors the microwave energy therebetween. The sensor component determines one or more of permittivity, conductivity, a change in permittivity, and a change in conductivity of the tissue between the first and second antennas. The sensor component can determine tissue temperature utilizing the monitored microwave energy and/or maps the microwave energy to a tissue temperature.

In another embodiment of the present disclosure, the system further includes a control component. The control component controls the generation of the microwave energy by the microwave output stage. The control component is in operative communication with the sensor component and operatively instructs the microwave output stage to generate the microwave energy until a monitored parameter in the monitored microwave energy reaches a predetermined threshold. The control component may be external to the microwave generator. The microwave output stage has a transmit mode and a receive mode. The microwave output stage generates the microwave energy when in the transmit mode and generates non-therapeutic or no microwave energy while in the receive mode. The control component controls the microwave output stage such that it is in one of the transmit mode and the receive mode (e.g., the transmit and receive modes of a particular microwave output stage may be mutually exclusive to each other). The control component instructs the microwave output stage to be in the transmit mode for a first period of time and in the receive mode for a second period of time. The sensor component receives microwave energy received by the first antenna when the microwave output stage is in the receive mode.

In another embodiment of the present disclosure, a microwave ablation system for treating tissue includes at least first and second antennas, first and second microwave output stages, first and second receivers, and a sensor component. The first and second antennas are adapted for insertion into tissue. The first microwave output stage generates a first microwave energy at a first frequency. The first microwave output stage is operatively coupled to the first antenna and is configured transmit the first microwave energy at the first frequency into the tissue. The second microwave output stage is adapted generate a second microwave energy at a second frequency. The second microwave output stage is operatively coupled to the second antenna and is configured to transmit the second microwave energy at the second frequency into the tissue.

The first receiver is operatively coupled to the second antenna and is adapted to receive the first microwave energy at the first frequency from the tissue. The second receiver is operatively coupled to the first antenna and is adapted to receive the second microwave energy at the second frequency from the tissue. The first and/or second receivers may be one of a circulator, an isolator, and/or a dual directional coupler. The sensor component is operatively coupled to the first and second antennas, and the first and second receivers. The sensor component is adapted to operatively monitor one or both of the first and second microwave energies between the first and second antennas. The system may further include a filter. The filter substantially filters the first microwave energy at the first frequency. The filter is operatively coupled between the sensor component and the first antenna to filter the first microwave energy of the first frequency therebetween. The first microwave output stage may generate the first microwave energy while the second microwave output stage generates the second microwave energy simultaneously for a first period of time.

In yet another embodiment of the present disclosure, a method of treating tissue includes: providing first and second antennas; inserting the first and second antennas into tissue; generating microwave energy; radiating the microwave energy from the first antenna through tissue; receiving the microwave energy with the second antenna from the tissue; and sensing the microwave energy between the first and second antennas. The method may further include estimating at least one of permittivity, conductivity, a change in permittivity, and a change in permittivity between the first and second antennas.

Additionally or alternatively, the method may include: determining a tissue temperature utilizing the sensed microwave energy and/or generating the microwave energy until a predetermined threshold is met. The predetermined threshold is one of permittivity of tissue, conductivity of tissue, a change in permittivity of tissue, a change in permittivity of tissue, permittivity between the first and second antennas, conductivity between the first and second antennas, a change in permittivity between the first and second antennas, and a change in permittivity between the first and second antennas. The method may further include: generating a test pulse of the microwave energy thereby sensing the microwave energy between the first and second antennas and/or radiating the microwave energy from the second antenna.

BRIEF DESCRIPTION OF THE DRAWINGS

These and other advantages will become more apparent from the following detailed description of the various embodiments of the present disclosure with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
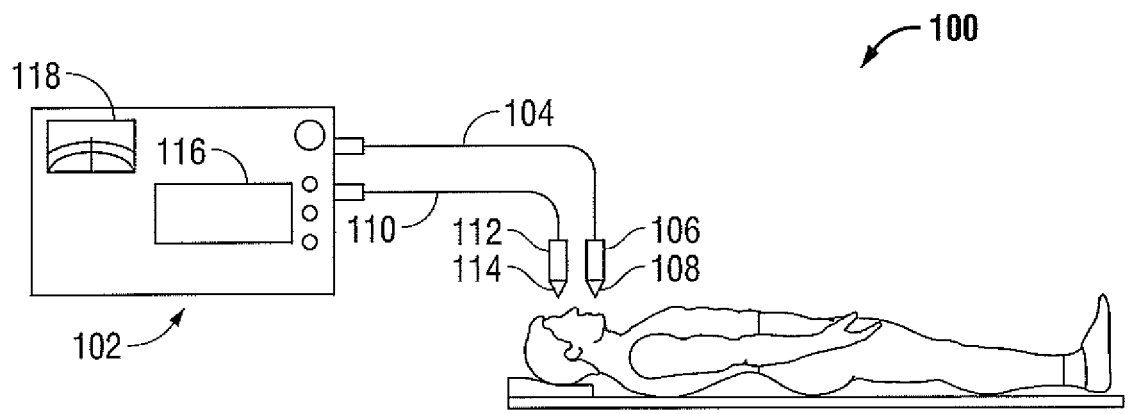
FIG. 1 is a schematic diagram of a microwave ablation system with tissue temperature monitoring in accordance with the present disclosure.

Referring to the drawings, FIG. 1 is a schematic diagram of a microwave ablation system 100 with tissue temperature monitoring in accordance with the present disclosure. Microwave system 100 includes a microwave generator 102 electrically coupled to a cable 104 that guides microwave energy to a surgical instrument 106. Surgical instrument 106 includes an antenna 108 that treats tissue of patient P. Microwave system 100 also includes a cable 110 that guides microwave energy to a surgical instrument 112 having an antenna 114 to treat tissue of patient P. Antennas 108 and 114 transmit microwave energy to tissue of patient P to ablate tissue when sufficient microwave energy is absorbed. In additional embodiments not depicted, more than two surgical instruments and/or more than two antennas may be used. Microwave generator 102 can measure tissue properties between antennas 108 and 114 to determine and/or estimate tissue temperature, treatment time, treatment completion and the like. Microwave generator 102 monitors one or more of permittivity and conductivity of the tissue between antennas 108 and 114, a change in permittivity and a change in conductivity of the tissue between antennas 108 and 114. Additionally or alternatively, microwave generator 102 determines tissue temperature utilizing the monitored microwave energy, e.g., microwave generator 102 maps a sensed parameter of the monitored microwave energy to a tissue temperature.

Microwave generator 102 includes a graphical user interface 116 and a dial indicator 118. Microwave generator 102 may also include other suitable input or output devices, such as knobs, dials, switches, buttons, displays and the like for control, indication and/or operation. Surgical instruments 106 and 112 may include buttons (not shown) that communicate with microwave generator 102 to generate the microwave energy. Microwave system 100 may also include a footswitch (not depicted) that connects to microwave generator 102. When actuated, the footswitch can cause microwave generator 102 to generate the microwave energy. Utilizing buttons on surgical instruments 106 and 112, or a footswitch enables the surgeon to activate the microwave energy while remaining near patient P regardless of the location of microwave generator 102.

Figure 2:
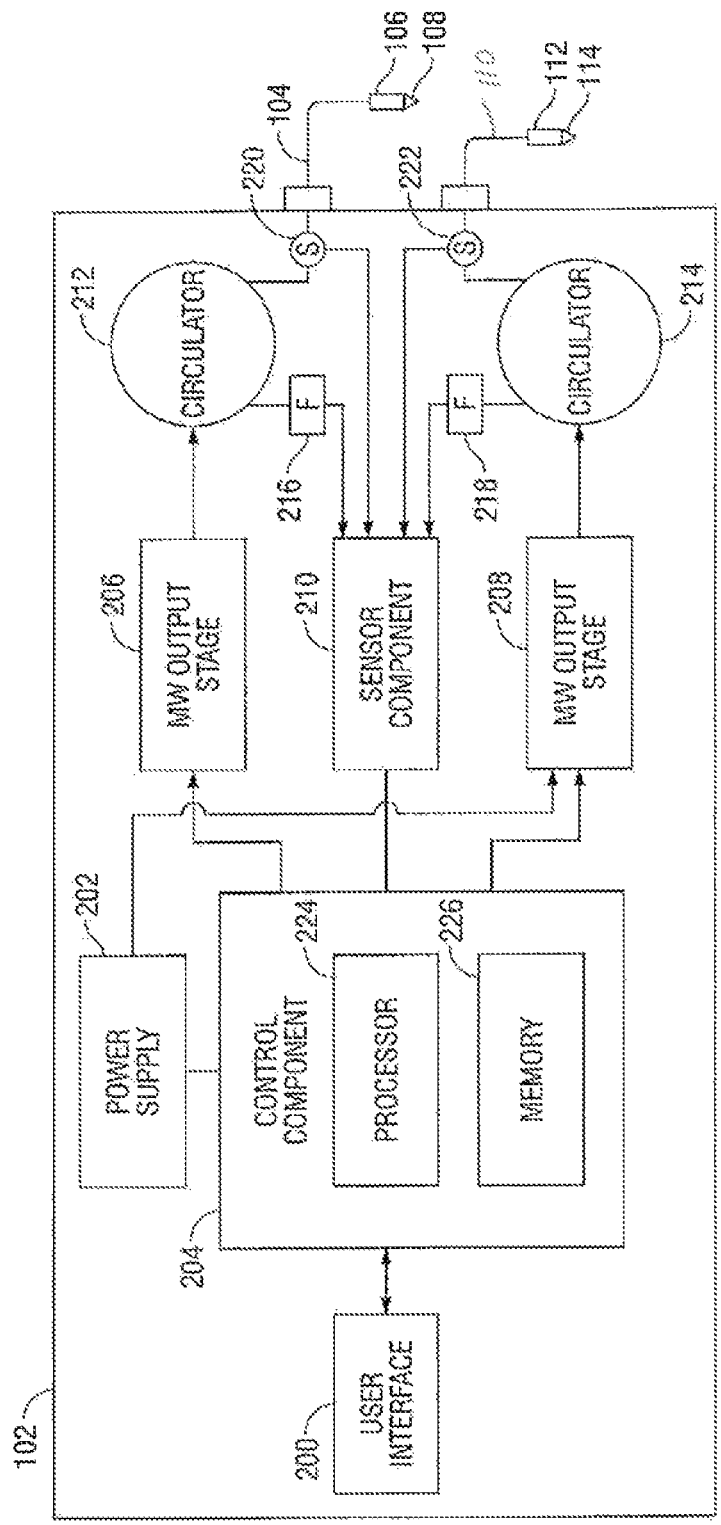
FIG. 2 is a schematic diagram of a microwave generator of FIG. 1 for use in accordance with the microwave ablation system according to the present disclosure.

Referring to the drawings, FIG. 2 is a schematic diagram of the microwave generator 102 of FIG. 1 in accordance with the present disclosure. Microwave generator 102 includes a user interface 200, a power supply 202, a control component 204, microwave output stages 206 and 208, and a sensor component 210. Sensor component 210 is coupled to circulators 212 and 213, through filters 216 and 218, respectively. Sensor component 210 is also coupled to sensors 220 and 222. Sensor 220 can measure forward and reflected power sent to antenna 108. Additionally, sensor 222 can measure forward and reflected power sent to antenna 114. Control component 204 includes processor 224 and memory 226. Sensor component 210 is coupled to control component 204 and communicates data relating to the monitored microwave energy between antennas 108 and 114 (discussed in more detail below).

Microwave generator 102 may be implemented wholly or partially in hardware, software, software in execution, bytecode, microcode, firmware, circuitry, a programmable logic device, the like, or some sufficient combination thereof. Microwave generator 102 may be connected to a network (e.g., the internet) and may include digital or analog connection devices, such as an RS-232 connection, an Ethernet connection or a GPIB connection, and the like.

Microwave generator 102 is controlled by control component 204. Control component 204 may also be referred to as a controller, a control module, and/or a controller board. Control component 204 includes processor 224 and memory 226. Processor 224 may be a microprocessor, a microcontroller, logic circuitry or a semiconductor-based logic device. Memory 226 may include program data, variables, stacks, heaps and the like Control component 204 may include communication interfaces such as serial bus interface and a parallel bus interface, and may also include related I/O buffers, flags or associated circuitry. Additionally, control component 204 may include analog-to-digital converters and/or digital-to-analog converters.

Control component 204 is in operative communication with user interface 200 and can receive user data therefrom. User interface 200 may also include mechanical or electrical interfaces, such as footswitches, switches, dials, screens, touch screens, speakers, microphones or the like, and associated circuitry. Control component 204 is in operative communication with power supply 202. Power supply 202 can receive instructions from control component 204 to supply microwave output stages 206 and 208 with sufficient power. Control component 204 may control microwave output stages 206 and 208 directly or indirectly through power supply 202.

Microwave output stages 206 and 208 can output microwave energy having a single wavelength, a plurality of wavelengths or a spectrum of wavelengths. The effective wavelength of antennas 108 or 118 may differ and may change based upon the surrounding tissue type, the surrounding tissue condition and/or the current progression of the ablation procedure. Microwave output stages 206 and/or 28 may change a wavelength of the microwave energy to "track" or "match" an effective wavelength of one or more of antennas 108 and 114. Power supply 202 provides the power for microwave output stages 206 and 208 while control component 204 controls the on/off times and/or the duty cycle. Control component 204 may utilize one or more modulation techniques to control the microwave energy, e.g., a pulse-width modulation technique. Alternatively, control component 204 may send a digital code to another semiconductor device (not shown), such as an ASIC chip, which generates the waveform for controlling the power supply 224.

Control component 204 may utilize feedback to control the generation of microwave energy, such as feedback measured by sensors 220 and 222, and processed by sensor component 210. Sensors 220 and 222 may be any sensor utilized in microwave systems, such as directional couplers. For example, sensors 220 and 222, in conjunction with sensor component 210, can measure microwave power output, an S-parameter, forward power, reflected power, and/or the like. Control component 224 may use the signal from sensor component 210 to control the generation of the microwave energy. The signal from sensor component 210 may be an analog or digital signal. For example, control component 204 may implement a feedback-type control algorithm using one or more signals from sensor component 210 as an "error" signal (such as in a PID algorithm) to determine what adjustments to make to the generated microwave energy. The error signal may correspond to microwave power being delivered.

Sensor component 210 determines tissue temperature utilizing the monitored microwave energy between antennas 108 and 114. Sensor component 210 can determine permittivity and conductivity of the tissue between antennas 108 and 114, and/or a change in permittivity and a change in conductivity of the tissue between antennas 108 and 114. Control component 204 maps the data received from sensor component 210. The measured parameters may be mapped to determine a tissue temperature. In another embodiment, sensor component 210 maps the data measured parameter and communicates the determined tissue temperature to control component 204. The control component 204 may control the generation of the microwave energy until a change in the monitored microwave energy reaches a predetermined threshold.

Microwave output stages 206 and 208, can have a transmit mode and a receive mode. When microwave output stage 206 is in a transmit mode, microwave output stage 208 is in a receive mode and a measurement of the tissue is made by sensor component 210. Additionally, when microwave output stage 208 is in a transmit mode, microwave output stage 206 is in a receive mode. When one of microwave output stages 206 and 208 is in a transmit mode, microwave energy is generated by the microwave output stage in transmit mode. When one of microwave output stages 206 and 208 is in a receive mode, non-therapeutic or no microwave energy is generated by the microwave output stage in receive mode. The receive mode of either microwave output stage 206 and/or 208 may be used to check the tissue properties, e.g., measure tissue parameters.

Consider the exemplary embodiment, control component 204 sets both of microwave output stages 206 and 208 to transmit mode to apply microwave energy to tissue for a few seconds. Control component 204 sets microwave output stage 206 to receive mode so that sensor component 212 receives the microwave energy transmitted from antenna 114 by receiving the microwave energy via antenna 108. Control component 204 sets microwave output stage 206 to the receive mode for a few tenths of a second. Sensor component 210 monitors the microwave energy therebetween while microwave output stage 206 is in receive mode. A tissue parameter is determined, and control component 204 sets microwave output stage back to transmit mode. After a few seconds, the control component 204 sets microwave output stage 208 to receive mode so that sensor component 212 receives the microwave energy transmitted from antenna 108 by receiving the microwave energy via antenna 114. Control component 204 sets microwave output stage 208 to the receive mode for a few tenths of a second, Sensor component 210 monitors the microwave energy therebetween while microwave output stage 208 is in receive mode. A tissue parameter is determined, and control component 208 sets microwave output stage back to transmit mode. Both microwave output stages 206 and 208 may be set to transmit mode about 95% of the time, or greater than 95% of the time. Control component 204 determines when the determined parameter reaches a predetermined threshold and stops treatment while issuing an alert to the user via user interface 200.

Circulators 212 and 214 direct microwave energy coming from the antennas 108 and 114 to sensor component 210, respectively. Additionally, circulators 212 and 214 direct microwave energy component from microwave output stages 206 and 208, to antennas 108 and 114, respectively. In other embodiments not depicted, microwave generator 102 can include an isolator, a dual directional coupler, and the like may be used in place of circulators 212 and/or 214.

In another embodiment of the present disclosure, tissue parameters are determined while microwave output stage 208 and 208 are both in transmit mode. Microwave output stage 208 transmits microwave energy at a first frequency and microwave output stage 208 transmits microwave energy at a second frequency. Filters 216 and 218 filter out the frequency from circulators 212 and 214, so that microwave energy that has traveling through tissue glow to sensor component 210 from filters 216 and 218, respectively.

Figure 3:
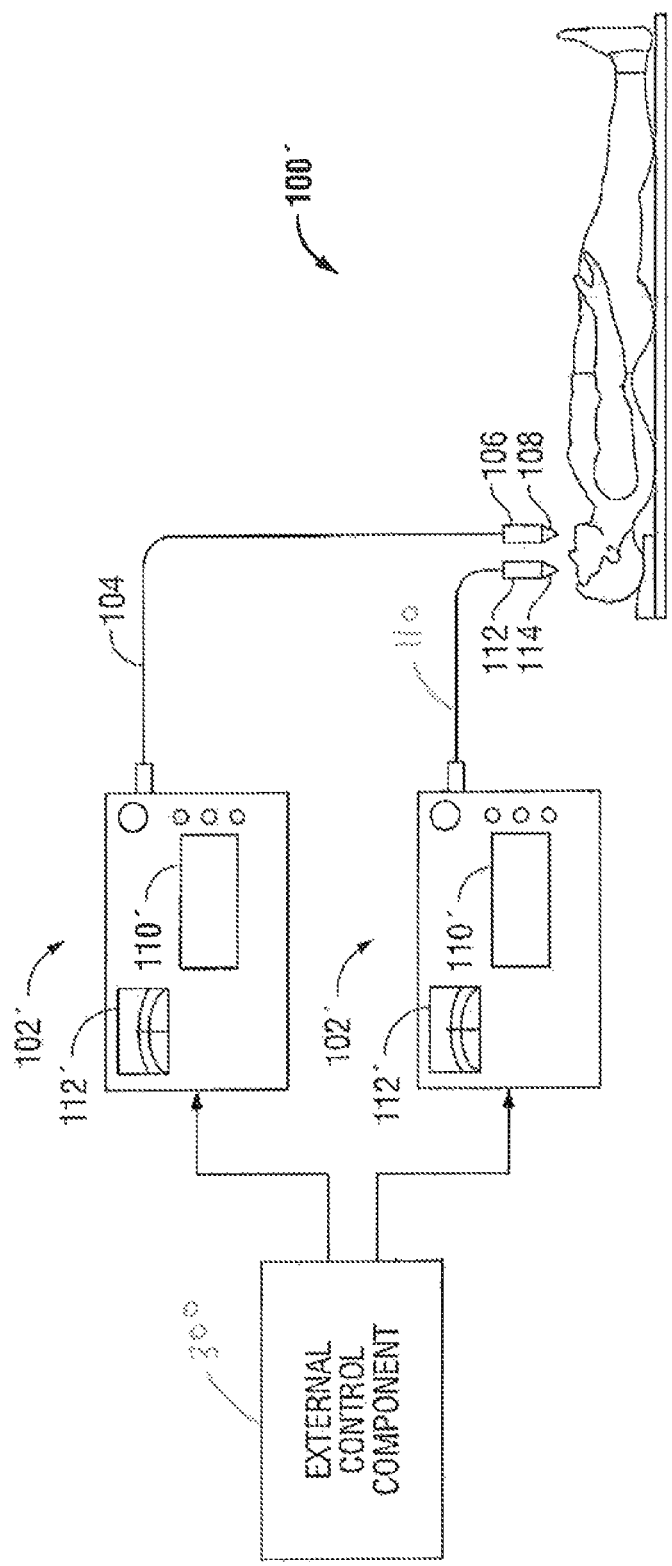
FIG. 3 is a schematic diagram of a microwave ablation system with tissue temperature monitoring having an external control component in accordance with the present disclosure.

Referring to the drawings, FIG. 3 is a schematic diagram of a microwave ablation system 100' with tissue temperature monitoring and having an external control component 300 in accordance with the present disclosure. External control component 300 is coupled to microwave generators 102'. External control component 300 controls the generation of microwave generators 102' so that tissue parameters may be determined similarly to microwave generator 102 of FIG. 1. For example, external control component 300 may instruct one of microwave generators 102' to generate microwave energy while receiving data from the other to determine permittivity and conductivity of the tissue between antennas 108 and 114, and/or a change in permittivity and a change in conductivity of the tissue between antennas 108 and 114. In one embodiment depicted in FIG. 3, the generators 102' may each have a transmit mode and a receive mode. The measured parameters may be mapped to determine a tissue temperature by external control component 300.

Figure 4:
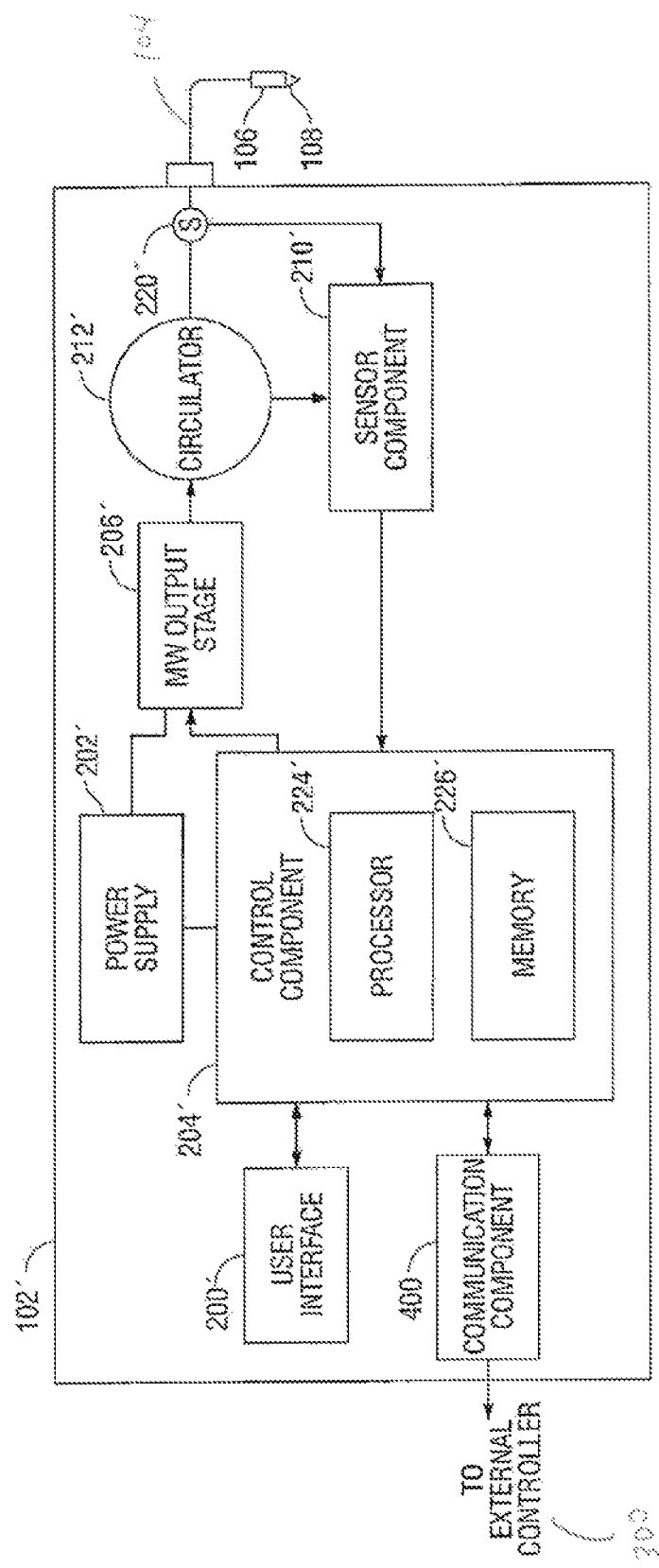
FIG. 4 is a schematic diagram of a microwave generator for use with the system of FIG. 3 in accordance with the present disclosure.

FIG. 4 is a schematic diagram of one of the microwave generators 102' of FIG. 3 in accordance with the present disclosure. Microwave generator 102' includes a user interface 200', a power supply 202', a control component 204', a microwave output stage 206', a sensor component 210', and a communications component 400. Sensor component 210' is coupled to circulator 212', through filter 214'. Sensor component 210' is also coupled to sensor 220'. Sensor 220' can measure forward and reflected power sent to antenna 108. Control component 204 includes processor 224 and memory 226.

The data collected from sensor component 210' is sent to communications component 400, which is in turn, is communicated to external controller 300 of FIG. 3. External controller 300 controls the generation of the microwave energy and measures the tissue parameters. External controller 300 may employ algorithms similar or identical to the one employed by microwave ablation system 100 of FIG. 1.

Sensor 220' measures forward and reflected power to antenna 108. The forward and reflected power is communicated to sensor component 210'. Sensor component 210' communicates the forward and reflected power to control component 226'. Control component 226' communicates the forward and reflected power to communication component 400 for communication to external controller 300 of FIG. 3.

Microwave energy received via antenna 108 (e.g., via antenna 114 of FIG. 4) is diverted to sensor component 210' by circulator 212' for measurement by sensor component 210'. Sensor component 210' can measure the power received, S-parameters, the frequency received, and the like. Sensor component 210' communicates the received microwave parameters to control component 226'. Control component 204' communicates the received microwave parameters to communication component 400 for communication to external control 300 of FIG. 3.

Figure 5A:
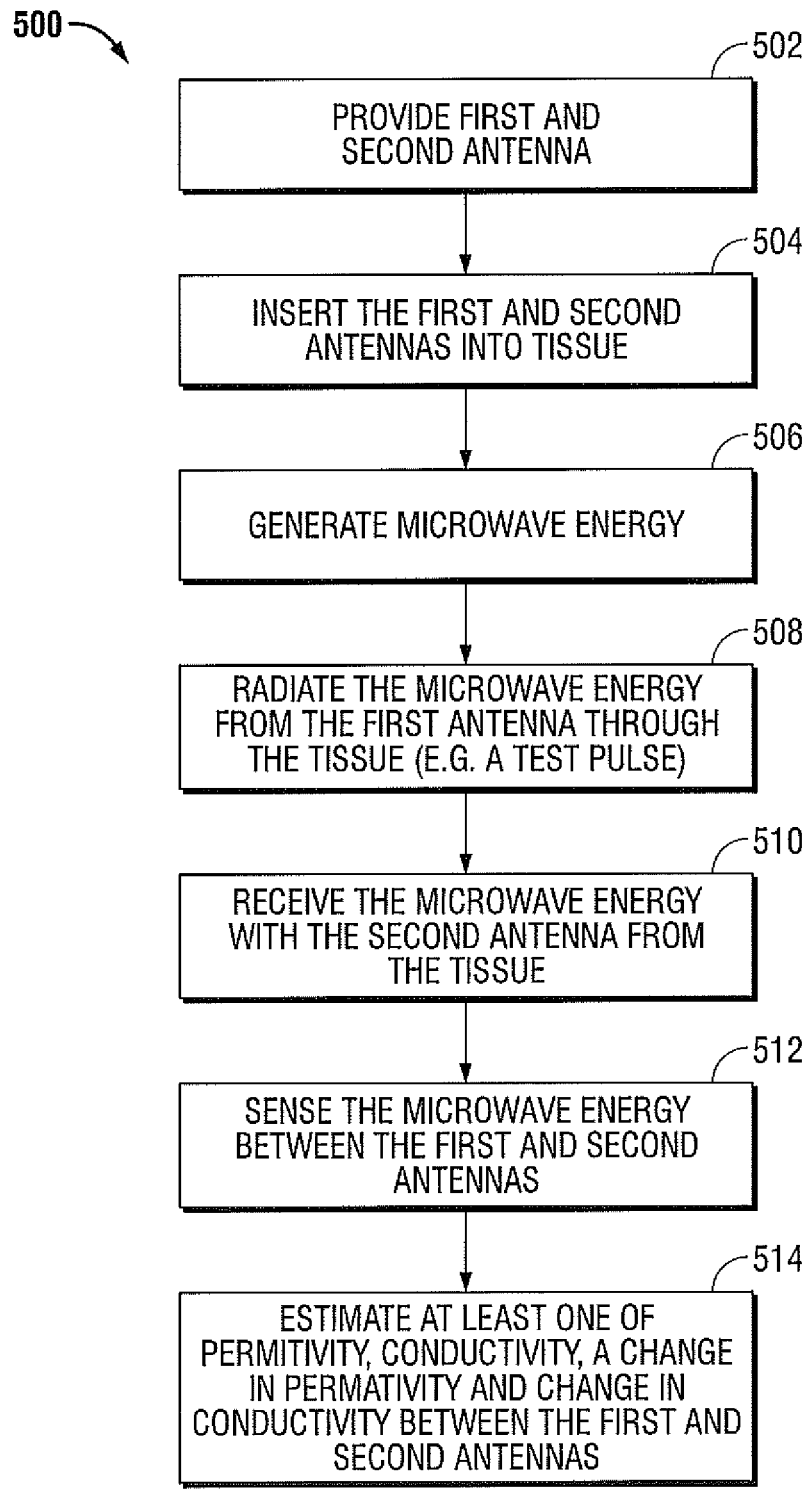
FIGS. 5A-5B are flow charts of a method for treating tissue with microwave energy while utilizing tissue temperature monitoring in accordance with the present disclosure.
Figure 5B:
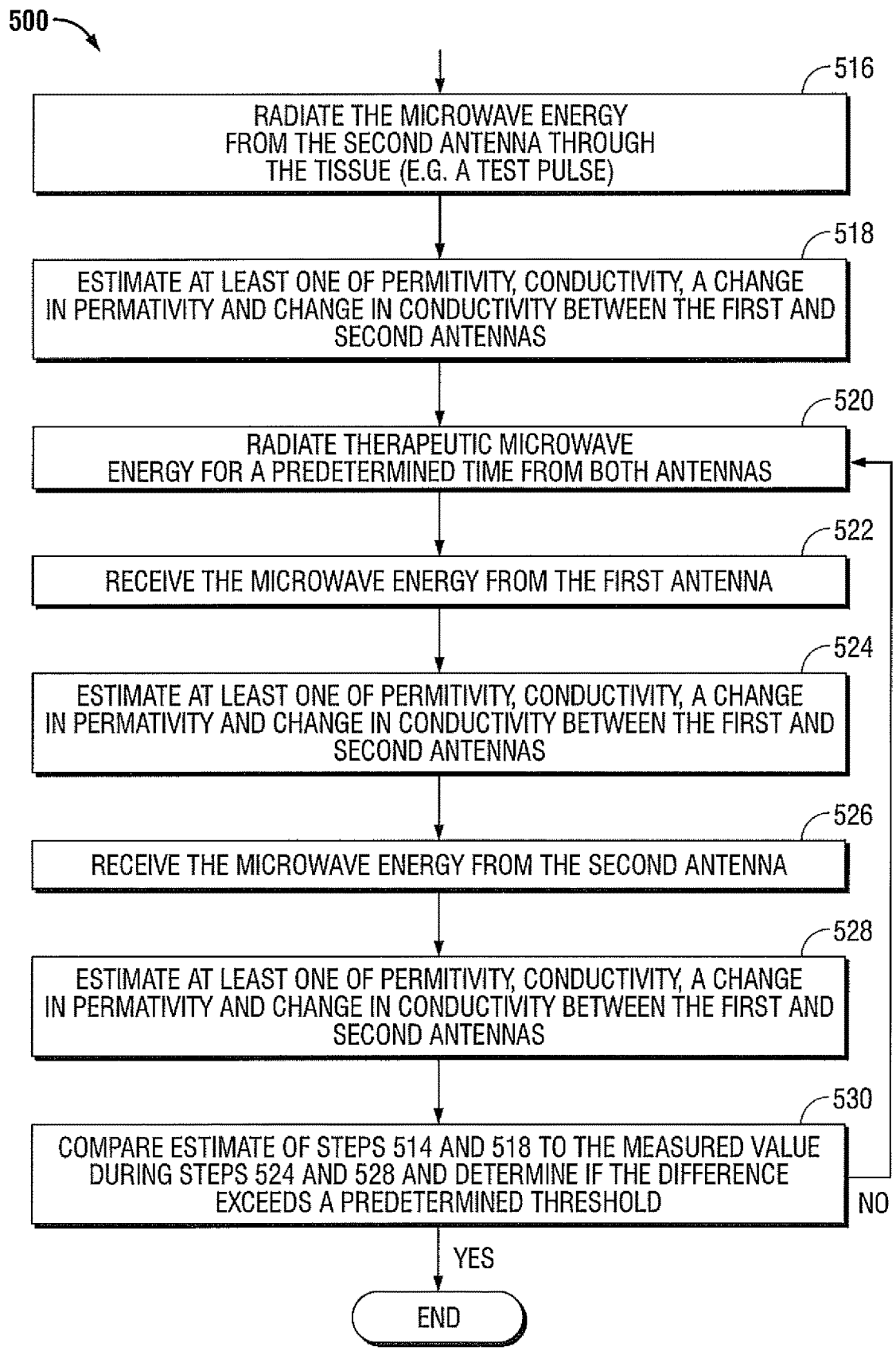

FIGS. 5A-5B is a flow chart diagram of a method 500 for treating tissue with microwave energy while utilizing tissue temperature monitoring in accordance with the present disclosure. Method 500 includes steps 502-530. Step 502 provides first and second antennas. Step 504 inserts the first and second antennas into tissue. Step 506 generates microwave energy. Step 508 radiates the microwave energy from the first antenna through the tissue (e.g., using a test pulse). Step 510 receives the microwave energy with the second antenna from the tissue. Step 512 senses the microwave energy between the first and second antennas. Step 514 estimates at least one of the permittivity, conductivity, a change in permittivity, and a change in conductivity between the first and second antennas.

Step 516 radiates the microwave energy from the second antenna through tissue (e.g., using a test pulse). Step 518 estimates one or more of the permittivity, conductivity, a change in permittivity, and/or a change in conductivity between the first and second antennas. Step 520 radiates therapeutic microwave energy for a predetermined time from both antennas (i.e., the first and second antennas). Step 522 receives the microwave energy from the first antenna. Step 524 estimates one or more of the permittivity, conductivity, a change in permittivity, and/or a change in conductivity between the first and second antennas.

Step 526 receives the microwave energy from the second antenna. Step 528 estimates one or more of the permittivity, conductivity, a change in permittivity, and/or a change in conductivity between the first and second antennas. Step 530 compares the estimates of steps 514 and 518 (e.g., an average of the two), to the estimates of steps 524 and 528 (e.g., the average of the two) and determines if the difference exceeds a predetermined threshold. If the differences do not exceed the predetermined threshold, method 500 continues to step 520. If the measured difference exceeds a predetermined threshold, treatment stops, enters into a standby stage, enters into other stages, and the like.

From the foregoing and with reference to the various figure drawings, those skilled in the art will appreciate that certain modification can also be made to the present disclosure without departing from the scope of the same. For example, other monitored characteristics may be utilized to estimate tissue temperature, such as impedance, S-parameters and the like.

What is claimed is:

1. A microwave ablation system for treating tissue, the system comprising:
    a first antenna for insertion into a first target tissue and a second antenna for insertion into a second target tissue;
    a first microwave output stage and a second microwave output stage each configured to generate microwave energy and to operate in a transmit mode and a receive mode, the first microwave output stage operatively coupled to the first antenna and the second microwave output stage operatively coupled to the second antenna, the first and second microwave output stages configured to generate the microwave energy when in the transmit mode and to generate non-therapeutic microwave energy when in the receive mode; and
    a sensor component operatively coupled to the first antenna and the second antenna and configured to operatively monitor at least one of permittivity or conductivity of tissue between the first antenna and second antenna as a function of the microwave energy therebetween;
    wherein the first microwave output stage controls the first antenna and the second microwave output stage controls the second antenna, and
    wherein the first antenna and the second antenna are orientationally maneuverable independent of each other for insertion into the first and second target tissues, respectively.

2. The system according to claim 1, wherein the sensor component determines at least one of a change in the permittivity or a change in the conductivity of tissue between the first antenna and the second antenna.

3. The system according to claim 1, wherein the sensor component determines a tissue temperature utilizing the microwave energy.

4. The system according to claim 1, wherein the sensor component maps the microwave energy to a tissue temperature.

5. The system according to claim 1, further comprising a control component for controlling the first and second microwave output stages while the first and second microwave output stages are in one of the transmit mode or the receive mode, wherein the control component is disposed in operative communication with the sensor component and operatively instructs the first and second microwave output stages to generate the microwave energy until a change in the microwave energy reaches a predetermined threshold.

6. The system according to claim 5, wherein the control component is external to a microwave generator having at least one of the first or second microwave output stages and the sensor component.

7. The system according to claim 1, wherein the sensor component receives the microwave energy received by the first antenna when the first microwave output stage is in the receive mode.

8. The system according to claim 1, wherein each of the first and second microwave output stages is operated in the transmit mode for a first period of time and operated in the receive mode for a second period of time.

9. The system according to claim 1, wherein when the first microwave output stage is in the transmit mode, the second microwave output stage is in the receive mode, and vice versa.

10. The system according to claim 1, wherein the first microwave output stage generates microwave energy at a first frequency and the second microwave output stage generates microwave energy at a second frequency.

11. The system according to claim 10, further comprising a first receiver operatively coupled to the second antenna for receiving microwave energy at the first frequency from the second target tissue.

12. The system according to claim 11, further comprising a second receiver operatively coupled to the first antenna for receiving microwave energy at the second frequency from the first target tissue.

13. The system according to claim 1, wherein the first and second microwave output stages are set to the transmit mode about 95% of the time.

14. The system according to claim 1, wherein a first circulator directs microwave energy from the first antenna to the sensor component and a second circulator directs microwave energy from the second antenna to the sensor component.

15. The system according to claim 1, wherein the first antenna is activated independently of the second antenna.

16. The system according to claim 1, wherein the first target tissue is different than the second target tissue.

17. The system according to claim 1, wherein the first antenna is coupled to a first surgical instrument and the second antenna is coupled to a second surgical instrument disposed separately from the first surgical instrument.

18. The system according to claim 1, further comprising:

a first surgical instrument configured to couple the first antenna to the first microwave output stage; and a second surgical instrument separate from the first surgical instrument and configured to couple the second antenna to the second microwave output stage.

* * * * *